United States Patent
Green et al.

(10) Patent No.: US 9,156,708 B2
(45) Date of Patent: *Oct. 13, 2015

(54) TAGGING SYSTEM AND METHOD

(75) Inventors: Darrell Green, Yarm (GB); Andrew West, Hartlepool (GB)

(73) Assignee: Johnson Matthey PLC, London (GB)

(*) Notice: Subject to any disclaimer, the term of this patent is extended or adjusted under 35 U.S.C. 154(b) by 115 days.

This patent is subject to a terminal disclaimer.

(21) Appl. No.: 13/424,851

(22) Filed: Mar. 20, 2012

(65) Prior Publication Data

US 2012/0184038 A1    Jul. 19, 2012

Related U.S. Application Data

(62) Division of application No. 12/064,760, filed as application No. PCT/GB2006/050251 on Aug. 22, 2006.

(30) Foreign Application Priority Data

Aug. 24, 2005   (GB) .................................... 0517258.0
Mar. 13, 2006   (GB) .................................... 0604904.3

(51) Int. Cl.
| | | |
|---|---|---|
| *G01N 37/00* | (2006.01) | |
| *C01C 1/08* | (2006.01) | |
| *F01N 3/20* | (2006.01) | |
| *G01N 21/64* | (2006.01) | |
| *G01N 21/78* | (2006.01) | |

(52) U.S. Cl.
CPC .............. *C01C 1/086* (2013.01); *F01N 3/2066* (2013.01); *G01N 21/643* (2013.01); *G01N 21/78* (2013.01); *F01N 2610/00* (2013.01); *F01N 2610/02* (2013.01); *Y02T 10/24* (2013.01); *Y10T 436/13* (2015.01)

(58) Field of Classification Search
CPC .................................................. G01N 33/2882
See application file for complete search history.

(56) References Cited

U.S. PATENT DOCUMENTS

| | | | |
|---|---|---|---|
| 3,634,038 A | | 1/1972 | Rampy |
| 4,040,787 A | * | 8/1977 | Roy et al. ...................... 436/108 |
| 5,132,096 A | | 7/1992 | Hoots et al. |
| 5,972,599 A | | 10/1999 | Tasset et al. |
| 7,100,367 B2 | | 9/2006 | Schaller et al. |

FOREIGN PATENT DOCUMENTS

| | | |
|---|---|---|
| EP | 0 584 915 A1 | 3/1994 |
| EP | 1 538 437 A1 | 6/2005 |
| FR | 2 843 612 A1 | 2/2004 |
| JP | 01-104199 | 4/1989 |
| JP | 02-104272 | 4/1990 |
| JP | 03-195499 | 8/1991 |
| JP | 5-107189 A | 4/1993 |
| JP | 6-116574 | 4/1994 |
| JP | 2001-020724 | 1/2001 |
| JP | 2002-085052 | 3/2002 |
| JP | 2003-503379 A | 1/2003 |
| JP | 2003-149231 | 5/2003 |
| JP | 2003-149231 A | 5/2003 |
| JP | 2003-529011 A | 9/2003 |
| JP | 2005-147989 A | 6/2005 |
| WO | WO-00/75643 A1 | 12/2000 |
| WO | WO 00/75643 A1 | 12/2000 |
| WO | WO 01/00561 A1 | 1/2001 |
| WO | WO-2004/025286 A1 | 3/2004 |

OTHER PUBLICATIONS

K.O. Lupetti et al., "An improved flow system for phenols determination exploiting multicommutation and long pathlength spectrophotometry," *Talanta*, vol. 62, Issue 3, Feb. 27, 2004, pp. 463-467.

ASTM D1783-01(2007) Standard Test Methods for Phenolic Compounds in Water.

Test Method 5530 D: Direct Photometric Method, Standard Methods for the Examination of Water and Wastewater, 19th edition, 1995, American Public Health Association, Library of Congress Catalog Card No. 95-79480.

Test Method 420.2: Colorimetric, Automated 4-AAP with Distillation, Methods for Chemical Analysis of Water and Wastes, Mar. 1983, United States Environmental Protection Agency, Office of Research and Development, Washington DC 20460.

AUS32 (AdBlue®) Specifications as per DIN70070, 2008.

Pilz et al., *Fresenius Journal of Analytical Chemistry*, 1965, vol. 212, No. 3, pp. 410-419.

* cited by examiner

*Primary Examiner* — Clinton Brooks
(74) *Attorney, Agent, or Firm* — RatnerPrestia

(57) ABSTRACT

A method of tracing an aqueous liquid, particularly an aqueous urea used for addition to a selective catalytic reduction system to remove NOx from diesel exhaust, includes adding a tracer comprising a pre-determined amount of a phenol to the liquid. The liquid can subsequently be identified by reacting a sample with a reagent containing a predetermined amount of 4-aminoantipyrine in the presence of an initiating compound such that the reaction between the reagent and a phenol in the liquid produces a chromophore and measuring the absorbance of the resulting solution of the chromophore.

21 Claims, No Drawings

TAGGING SYSTEM AND METHOD

CROSS-REFERENCE TO RELATED APPLICATIONS

This application is a divisional application of U.S. patent application Ser. No. 12/064,760, filed Feb. 25, 2008, which is the U.S. National Phase application of PCT International Application No. PCT/GB2006/050251, filed Aug. 22, 2006, and claims priority of British Patent Application No. 0517258.0, filed Aug. 24, 2005, and British Patent Application No. 0604904.3, filed Mar. 13, 2006, the disclosures of all of which are incorporated herein by reference in their entireties for all purposes.

FIELD OF THE INVENTION

The present invention relates to a tagging method for use in tagging an aqueous liquid, particularly a urea solution for use in selective catalytic reduction systems used to treat exhaust emissions, particularly exhausts from diesel engines.

BACKGROUND OF THE INVENTION

Heavy-duty diesel engines which are used largely in commercial vehicles are subject to increasing regulation of emission levels. It is therefore important to provide such engines with measures to reduce harmful emissions, especially particulates, and nitrogen oxides (NOx). Selective catalytic reduction (SCR) is a technology which has been introduced to reduce emissions of NOx by reducing the NOx to nitrogen. Ammonia-SCR systems react ammonia ($NH_3$) with the NOx to form nitrogen ($N_2$) and water ($H_2O$). There are three reaction pathways:

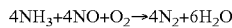

$$4NH_3+4NO+O_2 \rightarrow 4N_2+6H_2O$$

$$2NH_3+NO+NO_2 \rightarrow 2N_2+3H_2O$$

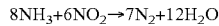

$$8NH_3+6NO_2 \rightarrow 7N_2+12H_2O$$

Any source of ammonia can be used but most commonly the source is an aqueous solution of urea. This decomposes in the exhaust stream in two stages to form ammonia and carbon dioxide ($CO_2$). The commercial standard form of urea sold for this purpose in Europe is a 32.5% aqueous urea solution, known as AdBlue™ which conforms to DIN 70070 standard for urea solution for use in SCR systems.

A concern with the introduction of such an additive is the control and monitoring of the use of suitable quality product which conforms to the accepted regulatory standard. With the introduction of mandatory emission control measures in many countries, the use of SCR technology will become regulated and therefore liable to inspection. Dilution of conforming Adblue or the use of Adblue from a non-conforming source should be capable of being monitored by the transport authorities' inspectors in order to ensure that vehicle emissions of NOx using SCR technology are suitably controlled. It is an object of the present invention to provide a tagging system for urea solutions for use in SCR systems and to provide a method of tagging urea and determining the source of a urea solution.

SUMMARY OF THE INVENTION

According to the invention we provide a urea solution, suitable for use in a process for the selective catalytic reduction of nitrogen oxides, said urea solution comprising a mixture of:

a) an aqueous solution of urea comprising from 30-35% of urea, b) a tracer composition comprising a phenol, optionally a secondary tracer compound and optionally a solvent.

According to a further aspect of the invention we provide a method of manufacturing a urea solution, suitable for use in a process for the selective catalytic reduction of nitrogen oxides, comprising adding to an aqueous solution of urea, comprising from 30-35% of urea, a tracer composition, said tracer composition comprising a phenol, optionally a secondary tracer compound and optionally a solvent.

According to a second aspect of the invention, we provide a method of identifying an aqueous liquid comprising the steps of:— a) mixing an aqueous liquid with a tracer composition comprising at least one phenol to form a tagged aqueous liquid, and b) analysing a sample of said tagged aqueous liquid by reacting said sample with a reagent containing a pre-determined amount of 4-aminoantipyrine in the presence of an initiating compound such that the reaction between the reagent and a phenol in the liquid produces a chromophore and c) measuring the absorbance of light of the resulting solution of the chromophore to determine the concentration of said tracer compound.

According to a further aspect of the invention, we provide a method of comparing a target sample of an aqueous liquid with a reference sample of a similar aqueous liquid comprising the steps of:— a) mixing a pre-determined quantity of a tracer composition comprising at least one phenol with a measured volume of said aqueous liquid to form a tagged aqueous liquid, b) reacting a reference sample of said tagged aqueous liquid with a reagent containing a predetermined amount of 4-aminoantipyrine in the presence of an initiating compound such that the reaction between the reagent and a phenol in the liquid produces a chromophore, and measuring the absorbance of light of the resulting solution of the chromophore prepared from the reference sample c) reacting a target sample of a similar aqueous liquid with a reagent containing a pre-determined amount of 4-aminoantipyrine in the presence of an initiating compound such that the reaction between the reagent and a phenol in the liquid produces a chromophore, measuring the absorbance of light of the resulting solution of the chromophore prepared from the target sample d) comparing the absorbance of light of the resulting solution of the chromophore prepared from the target sample with the absorbance of light of the resulting solution of the chromophore prepared from the reference sample to determine the similarity of the target sample to the reference sample.

In the comparison method, it is not necessary to determine the absorbance of light of the resulting solution of the chromophore prepared from the reference sample each time a target sample is analysed. It may be convenient to compare the light absorbance from a solution prepared from the target sample with a pre-determined absorbance measurement from a standard reference sample. This absorbance measurement may be programmed into a measurement instrument which is adapted to facilitate the comparison of a target sample with a standard reference. In steps b) and c) of the comparison method it is optionally provided that the concentration of the tracer compound in the target and/or reference sample is calculated from the absorbance measurement, usually by comparison with a calibration of the absorbance using known standard concentrations of the tracer compound. It is not necessary for the calculation of the concentration of tracer compound to be performed if the comparison method is performed in order to determine whether the target sample contains the tracer compound at a concentration similar or identical to the tracer concentration in the reference compound.

In a still further aspect of the invention, an identification system for the comparison of a target sample of an aqueous liquid with a reference sample of a similar tagged aqueous liquid comprises:
(i) a tracer composition comprising at least one phenol; and
(ii) pre-determined amount of 4-aminoantipyrine
(iii) an initiating compound for the coupling reaction between the 4-aminoantipyrine reagent and said at least one phenol to produce a solution of a chromophore
(iv) a reaction vessel to contain said 4-aminoantipyrine, said initiating compound and said sample during their reaction to produce said solution of a chromophore; and
(v) a portable analytical apparatus, comprising
   (a) a colorimeter or spectrophotometer capable of measuring the absorbance of said solution of said chromophore;
   (b) data-processing means for comparing the absorbance of the solution of chromophore formed by the reaction of the target and reference samples with the reagent and
   (c) an indication means for indicating whether the concentration of the tracer compound in the target sample and the reference sample differ by more than a pre-determined amount.

According to a further aspect of the invention, a method of tracing an aqueous liquid comprises adding to said liquid a tracer comprising a pre-determined amount of a phenol, subsequently sampling said liquid, reacting said sample with a reagent containing a pre-determined amount of 4-aminoantipyrine in the presence of an initiating compound such that the reaction between the reagent and a phenol in the liquid produces a chromophore and measuring the absorbance of the resulting solution of the chromophore.

DETAILED DESCRIPTION OF THE INVENTION

By "tagged aqueous liquid" we mean an aqueous liquid which has been modified by mixing with a measured amount of the tracer composition.

By "reference sample" we mean a sample of a tagged aqueous liquid which contains a known concentration of the tracer composition.

By "target sample" we mean a sample of an aqueous liquid which contains an unknown amount or none of the tracer composition.

The urea solution preferably comprises a 32.5% aqueous solution of urea in accordance with the DIN70070 standard (of August 2005) for urea solutions for SCR systems to reduce emissions of nitrogen oxides from diesel engines, known commercially as AdBlue®.

By tracing a liquid we mean providing the liquid with an identifying tracer and then subsequently analysing a sample of the liquid (the target sample) to identify the tracer, compare the concentration of tracer to that of a reference sample and thus determine whether the liquid sampled is substantially the same as the liquid to which the tracer was added. Normally the tracer is added to the liquid during its manufacture. When the liquid is for distribution and it is required to be traced through the distribution channels, the tracer is added prior to distribution. When the liquid is AdBlue, the tracer is preferably added prior to the distribution of the liquid by the manufacturer to wholesale and retail outlets, e.g. fuel suppliers and forecourts.

The tracer may be a liquid or a solid but it must be soluble in or miscible with the aqueous liquid. The tracer is a phenol, i.e. phenol or a substituted phenol. Suitable substituted phenols include alkyl phenols e.g. 2-methyl phenol, 2-ethylphenol, alkoxy phenols e.g. 3-ethoxy phenol; hydroxy-phenols, e.g. catechols, hydroquinone. It is preferred that the phenol is not para-substituted with an alkyl, aryl, nitro, benzoyl, nitroso or aldehyde group. The concentration of the phenol in the aqueous liquid is preferably in the range from 0.1-20 ppm w/v.

The amount of tracer in a sample of the aqueous liquid is preferably determined by a spectrophotometric method involving the coupling reaction between the phenol and 4-aminoantipyrine. Alternative methods may be used, such as the coupling of the phenol with 3-methyl-2-benzothiazole hydrazone, which is a known analytical method for the determination of phenol in water. The coupling of phenols with 4-aminoantipyrine to form a chromophore is a well-known analytical method to measure the amount of phenols in wastewater or for use in enzymatic methods for analysis of body fluids, e.g. the determination of cholesterol in blood. The method of such analysis is therefore well known to the skilled person. A description of such methods is found in Lupetti et al., Talanta 62 (2004) 463-467; ASTM D1783 Test method B; APHA Standard Method 5530D and EPA Methods for Chemical Analysis of Water and Wastes, Method 420.2.

The coupling of phenols with 4-aminoantipyrine (4-AAP) to form a chromophore takes place in alkaline solution in the presence of an initiator. The coupling reaction requires one mole of 4-AAP per mole of phenol. The 4-aminoantipyrine solution is normally aqueous and may contain from about 0.5 to about 30 g per liter, more preferably from about 1-20 g per liter. The amount of 4-aminoantipyrine used should be sufficient to couple all of the phenol in the sample and is preferably present in sufficient amount to provide an excess of 4-AAP e.g. at least 1.5 moles of 4-AAP per mole of phenol, e.g. from about 2 to about 5 moles of 4-AAP per mole of phenol. Since the amount of phenol expected to be present in the sample is known (because the amount of tracer added to the aqueous liquid is known) it is possible to calculate the required amount and concentration of 4-AAP reagent to be used. The pH is preferably in the range from 9.8 to 10.2.

The initiating compound is used at a concentration sufficient to initiate the coupling of the 4-aminoantipyrine with a phenol to form a chromophore. The initiating compound may be potassium ferricyanide. Normally from about 1 mole to at least 2 moles of potassium ferricyanide are provided per mole of 4-aminoantipyrine. The concentration of potassium ferricyanide in the coupling solution is preferably in the range from about 0.05% to about 2%, typically about 0.1% w/v. We have found that the presence of free ammonia at a concentration greater than about 100 ppm in the sample may give rise to problems with the analysis if potassium ferricyanide is used as the initiator. In such cases, or where the presence of ammonia is likely, an alternative initiator, which preferably comprises a persulphate, especially sodium persulphate, may be used. The persulphate should be present in the solution at a sufficient concentration to oxidise the 4-AAP reagent, and this is preferably an amount sufficient to provide a concentration in the range from about 0.5% to about 10%, typically about 1% w/v. The initiator may conveniently be added to the sample of aqueous liquid in the form of a pre-weighed solid unit such as a pill or tablet or in a powdered form of the initiator compound, preferably in a pre-measured dose in a container, sachet or ampoule. In a particularly preferred form, the initiator is provided either in powdered form or in the form of compressed tablets in a dispenser-container which is adapted to dispense a pre-determined amount of the initiator when the dispenser is actuated. It should be noted that, provided the amount of initiator is at least sufficient, it is not critical that a precise amount is dispensed. As an alternative, the initiator may be provided within or disposed on a portion of an ampoule containing the 4-AAP reagent. This arrangement is found on commercial analysis kits.

The chromophore exhibits strong absorbance of light in the region 500-510 nm. The absorbance is proportional to the concentration of the chromophore in the solution, according to the Beer-Lambert law and the absorbance is therefore proportional to the concentration of phenol in the sample. Changes in the absorbance of the solution at a specified wavelength in the range from 500 to 510 nm from that exhibited by the aqueous liquid when the tracer compound had been added indicate that the liquid sample has been diluted or otherwise changed from its original composition.

The presence of the chromophore and its concentration is preferably measured using a colorimeter or spectrophotometer. In a preferred embodiment of the method of the invention, the colorimeter or spectrophotometer is a portable, preferably hand-held instrument, i.e. capable of being held and operated in the hand of the user. To facilitate the measurement using a small instrument, in this embodiment, the absorbance of the sample in the region 500-510 nm is preferably measured at one or more pre-determined wavelengths within this range rather than measuring a broad spectrum of transmitted light. The preferred photometer instrument preferably comprises a sample chamber for holding the sample during a photometric measurement, means for irradiating a sample in the sample chamber with light of a pre-determined wavelength in the region from 500-510 nm, means for detecting the transmission of light at said wavelength which has passed from the irradiating means through the sample chamber and means for determining the absorbance of said light by the sample and display means for indicating said absorbance or a value calculated from said absorbance.

The means for irradiating the sample chamber may be a broad spectrum source coupled with a filter. Alternatively a narrow spectrum source such as a laser or a light-emitting diode may be used.

The hand-held instrument is preferably pre-calibrated, i.e. programmed with one or more calibration curves relevant to the detection of the chromophore formed by coupling the phenol tracer with 4-aminoantipyrine. The calibration may be made using the particular phenol to be used in the tracer or it may be made using a different phenol. If made using a different phenol then the analysis result may be adjusted by a factor which accounts for the difference between the response of the method using the calibration phenol and that using the tracer phenol. It has been found that the calibration of the instrument may vary according to the temperature at which the absorbance is measured. Therefore, it is beneficial for the instrument to be capable of using a calibration which is suitable for use at the temperature of the sample. The hand-held instrument is preferably provided with means to monitor the temperature of the sample being analysed. This may be by means of a probe or temperature-reactive chemical for example. The instrument may be provided with means for a user to input the temperature of the sample directly. Alternatively the instrument may provide a facility for the user to select the calibration curve which is to be used. More preferably, the instrument is capable of applying the appropriate calibration depending on the temperature as measured by the instrument or as input by the user.

The hand-held instrument is preferably provided with software and a user interface which is adapted to provide a direct reading of the concentration of phenol calculated from the absorbance of the chromophore. The absorbance exhibited by a chromophore formed by the coupling of a substituted phenol is normally less than that of the chromophore formed by phenol itself. The result from such substituted phenols may be expressed as "phenol equivalents", i.e. showing the concentration of phenol which would give rise to the equivalent absorbance at similar wavelengths. More preferably, the user interface provides a direct reading of the difference between the concentration of phenol in the measured sample and the concentration of phenol in a standard sample so that the user is alerted to a difference in the aqueous liquid from the standard. Using this preferred embodiment, the liquid may be analysed for the presence and concentration of the tracer phenol at the point of sampling by personnel who are not trained analysts. The output information may be shown on a display and/or printed, e.g. using an integral printer. The colorimeter or photometer (the instrument) is preferably provided with a user interface which allows the input of a sample identifier. The instrument preferably includes a clock function to record the date and time of analysis. The display may comprise a conventional visible indication such as a light, display screen or printout. Additionally or alternatively an audible signal may be used. As a further addition or alternative, the system may comprise a data transmission means whereby the results for a particular sample are transmitted, e.g. by known telephone or radio transmission means to a remote location together with supporting information such as the time and location of the sampling and analysis, sample identifier etc. Such transmission may optionally be automatically carried out when a comparison is made.

The 4-aminoantipyrine reagent, containing a suitable solvent, buffer solution etc is preferably provided in a pre-determined quantity within a sealed container, the quantity being sufficient to perform a single test. The sealed container may be an ampoule, test-tube or bottle, but is preferably a self-filling ampoule, containing the reagent and which, in operation, may be filled with a pre-determined amount of the liquid to be sampled. The preferred ampoules containing the reagent include an evacuated space and a breakable tip portion. When the tip is immersed in the liquid to be sampled and broken, a quantity of liquid is drawn into the ampoule and mixed with the reagent. Such ampoules are described in U.S. Pat. No. 3,634,038, for example and are commercially supplied as Vacu-vials®. Suitable ampoules containing the 4-aminoantipyrine reagent are commercially available for the analysis of phenols and are suitable for use in the method of the present invention. A specific form of one such ampoule incorporates a pre-determined amount of the initiator compound on the external surface of the tip of the ampoule so that it is readily mixed into the sample before the sample is mixed with the 4-AAP reagent in the ampoule.

The tracer composition may optionally contain one or more additional tracer compounds which are detectable by standard analytical procedures. The additional tracer compound may, for example comprise a dye, or other compound which is not a natural or usual component of the aqueous liquid to which the tracer composition is to be added but which is soluble in the aqueous liquid at the levels used.

The additional tracer compound may comprise a dye which is detectable by visible or by spectroscopic analysis. Preferred dyes are not visible to the eye but are detectable only by spectroscopic means. Preferably the dye is a fluorescent dye which is detectable by fluorimetry/fluorescence spectroscopy. Most preferably the selected dye fluoresces at a peak wavelength which is distinguishable from the fluorescence of the natural components of the aqueous liquid, when irradiated with light at a wavelength capable of exciting fluorescence in the dye. Suitable dyes are known in the art of tracers and include xanthenes, phthalocyanines, naphthalocyanines, nickel-dithiolane complexes, cyanines, porphyrins, 16,17-dialkoxyviolanthrones, alkylated dibenzanthrone, anthraquinones and squarines, rhodamines and oxazines, amongst others.

Alternative additional tracer compounds may, for example comprise a halogenated organic compound, or other compound which is not a natural or usual component of the aqueous urea product to which the marker composition is to be added. Suitable halogenated compounds include halogenated aliphatic or aromatic compounds, such as bromoethanol, iodopropanol, 3-bromobenzoic acid, 4-fluorobenzoic acid, 2-bromobenzylamine, 2-bromo-4-chloroaniline, perfluorohetanoic acid, 1H,1H,2H,2H-perfluorooctanol, perfluorotri-n-butylamine and/or fluoroamine. Non-halogenated marker compounds may comprise, for example, one or more of the following:—butan-2-ol, propanone, 1,3-propanediol, aminophenol, aminophenone, aminobenzoic acid, pyridine or pyrimidine or phosphorus-containing compounds such as an alkyl or aryl phosphate, e.g. triethyl phosphate.

When the tracer composition comprises more than one tracer compound and/or additional tracer compound, the ratio of each tracer compound to each other tracer compound in the tracer composition may be selected to be a unique identifier for each aqueous liquid or source of aqueous liquid to be tagged. Thus by selection of the nature and concentration of each tracer compound in a tracer composition, the aqueous liquid, when tagged may bear a unique "fingerprint" which may be used to identify product in a way which is difficult for a non-authorised person to replicate. One particular use for the combination of tracers is for the identification of particular batches of the aqueous liquid, e.g. for verification of the date of manufacture to ensure that the product is sold within the shelf-life of the aqueous liquid.

The additional tracer compound may be analysed by any suitable method. It is not necessary for the additional tracer to be identified "in the field" since it is used to confirm the analysis of the phenol tracer in case a discrepancy from the expected result is found or tampering is suspected. Thus the additional tracer may be detectable using spectroscopic methodology, e.g. infra-red spectroscopy, fluorimetry, mass spectrometry, NMR spectroscopy, chromatography, e.g. gas-chromatography, optionally coupled with a suitable detector or by comparison with standard chromatograms.

The tracer composition may optionally contain, in addition to the tracer compound (or more than one tracer compound), one or more other components such as a diluent, a solvent, a dye, a dispersant, or a surfactant. The identity and amount of the components of the tracer composition is normally confidential to the source producer of the product. The tracer composition is preferably a liquid but may also be provided in solid form if it is capable of being dissolved in the aqueous liquid without difficulty. If provided in solid form then additives may be present to enhance and facilitate the dissolution of the tracer composition in the aqueous liquid.

The method and system of the invention are particularly useful for marking, identifying and tracing aqueous liquids through the supply chain from source to consumer. Thus the method and system of the invention may be used to identify a genuine product when there is a risk of adulteration or of substitution with a similar product. Thus aqueous liquids in which the tracer composition may be used include aqueous urea solutions, aqueous process streams, consumer products such as cleaning products etc. The method and system of the invention is particularly suitable for tagging and identifying genuine Ad Blue urea solution for use in heavy duty and lighter diesel engine SCR apparatus. The marking of an aqueous liquid may, alternatively, be used to trace the source of a spillage or for process monitoring applications.

EXAMPLES

The method of the invention is further described in the following examples.

Example 1

0.1 grams of phenol was accurately weighed and diluted with 100 grams of water to produce a stock solution of a tracer composition. 1 ml of the tracer composition solution is added to 100 ml of a 32.5% w/v aqueous urea solution, to produce a 10 ppm w/v phenol tracer/urea solution.

Analysis of this sample was performed using a Jenway 6100 Spectrophotometer set to analyse at a wavelength of 505 nm. An initial manual calibration of the instrument was performed using seven standards within the concentration range of 0 to 15 ppm w/v at 0, 2.5, 5, 7.5, 10, 12.5 & 15. All standards were produced from the 0.1% w/v stock solution of phenol material. The technique for the formation of the colour complex to be determined is described below.

Approximately 25 ml sample of each phenol tracer/urea solution was placed into a glass vial containing approximately 0.03 grams of Potassium Ferricyanide. In a separate glass vial a 2 ml aliquot of 0.005M 4-aminoantipyrine was discharged. 4.5 ml of the phenol solution from the first vial was then transferred into the vial containing 4-aminoantipyrine. The resulting red coloured solution, a consequence of an oxidative coupling reaction, was added to a suitable cuvette for photometric analysis. A calibration plot of absorbance vs concentration was drawn and it was hence possible to determine the concentration of the initial 10 ppm w/v phenol tracer/urea solution.

Example 2

10 grams of triethyl phosphate was accurately weighed and diluted with 100 ml of ethanol to produce a stock solution of secondary tracer composition. 2 ml of the tracer composition solution is added to 1000 ml of a 32.5% w/v aqueous urea solution, to produce a 200 ppb w/v secondary tracer/urea solution. The sample was pre-concentrated on an Isolute™ ENV+SPE column and eluted using acetone. Analysis of this sample was performed by gas chromatography (Agilent 6890) coupled with a Mass Selective Detector (Agilent 5973) set up for chemical ionisation of the target molecule. The column and conditions used were:

GC column: 100% dimethylpolysiloxide 15 meter*0.25 mm*0.25 µm film thickness (Varian™

VF-1)

GC oven temperature: 500 C ramped up to 1300 C over an 8 minute run. The temperature can be ramped up quickly over a shorter time frame to reduce the analysis run time, however the starting temperature should not exceed 1000 C in order to achieve good column loading. Carrier gas (H2) flow rate: 2 ml per minute.

Example 3

0.1 grams of phenol was accurately weighed and diluted with 100 grams of water to produce a stock solution of a tracer composition. 1 ml of the tracer composition solution is added to 100 ml of a 32.5% w/v aqueous urea solution, to produce a 10 ppm w/v phenol tracer/urea solution. Analysis of this sample was performed using a Jenway 6100 Spectrophotometer set to analyse at a wavelength of 505 nm. An initial manual calibration of the instrument was performed using seven standards within the concentration range of 0 to 15 ppm w/v at 0, 2.5, 5, 7.5, 10, 12.5 & 15. All standards were produced from the 0.1% w/v stock solution of phenol material. The technique for the formation of the colour complex to be determined is described below. Approximately 25 ml sample of each phenol tracer/urea solution was placed into a glass vial containing approximately 0.25 grams of sodium persulphate. In a separate glass vial a 2 ml aliquot of 0.005M 4-aminoantipyrine was discharged. 4.5 ml of the phenol solution from the first vial was then transferred into the vial containing 4-aminoantipyrine. The resulting red coloured solution, a consequence of an oxidative coupling reaction, was added to a suitable cuvette for photometric analysis. A calibration plot of absorbance vs concentration was drawn and it was hence possible to determine the concentration of the initial 10 ppm w/v phenol tracer/urea solution.

What is claimed:

1. A method of identifying an aqueous liquid comprising the steps of:
   a) mixing an aqueous liquid with a tracer composition comprising a tracer to form a tagged aqueous liquid;
   b) analysing a sample of said tagged aqueous liquid by reacting said sample with a reagent containing a pre-determined amount of 4-aminoantipyrine in the presence of an initiating compound such that the reaction between the reagent and the tracer in the liquid produces a chromophore; and
   c) measuring an absorbance of light of the resulting solution of the chromophore to determine the concentration of said tracer,
   wherein the tracer has the following structure:

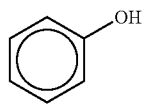

and any of carbon numbers 2-6 of the phenyl group may optionally be substituted.

2. A method according to claim 1, wherein the light has a wavelength between 500 and 510 nm.

3. A method according to claim 2, further comprising the step of comparing the concentration of the tracer in the sample with a concentration of tracer in a reference sample to determine the similarity of the sample to the reference sample.

4. A method according to claim 3, wherein said comparison is carried out by comparing the absorbance of light at a wavelength between 500 and 510 nm of the chromophore solution made from the sample with a chromophore solution formed from the reference sample under the same conditions.

5. A method according to claim 1, wherein said aqueous liquid comprises an aqueous solution of urea comprising from 30-35% of urea.

6. A method according to claim 5, wherein said aqueous solution of urea comprises a 32.5% aqueous solution of urea in accordance with the DIN70070 standard for urea solutions for SCR systems.

7. A method according to claim 1, wherein said phenol is selected from the group consisting of phenol, an alkyl phenol, an alkoxy phenol, a hydroxyphenol, and mixtures thereof.

8. A method of comparing a target sample of an aqueous liquid with a reference sample of a similar aqueous liquid comprising the steps of:
   a) mixing a pre-determined quantity of a tracer composition comprising at least one tracer with a measured volume of said aqueous liquid to form a tagged aqueous liquid;
   b) reacting a reference sample of said tagged aqueous liquid with a reagent containing a predetermined amount of 4-aminoantipyrine in the presence of an initiating compound such that the reaction between the reagent and the tracer in the liquid produces a chromophore, and measuring the absorbance of light of the resulting solution of the chromophore prepared from the reference sample;
   c) reacting a target sample of a similar aqueous liquid with a reagent containing a pre-determined amount of 4-aminoantipyrine in the presence of an initiating compound such that the reaction between the reagent and the tracer in the liquid produces a chromophore, measuring the absorbance of light of the resulting solution of the chromophore prepared from the target sample; and
   d) comparing the absorbance of light of the resulting solution of the chromophore prepared from the target sample with the absorbance of light of the resulting solution of the chromophore prepared from the reference sample to determine the similarity of the target sample to the reference sample,
   wherein the tracer has the following structure:

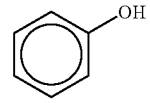

wherein any of carbon numbers 2-6 of the phenyl group may optionally be substituted.

9. A method of analyzing a sample of a urea solution comprising the steps of:
   a) reacting said sample with a reagent containing a pre-determined amount of 4-aminoantipyrine in the presence of an initiating compound such that the reaction between the reagent and a tracer compound present in the liquid produces a chromophore; and
   b) measuring the absorbance of light of the resulting solution of the chromophore to determine the concentration of said tracer compound
   wherein said tracer compound has the following structure:

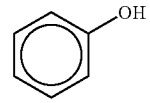

wherein any of carbon numbers 2-6 of the phenyl group may optionally be substituted.

10. A method as claimed in claim 9, wherein the light has a wavelength between 500 and 510 nm.

11. A method as claimed in claim 9, further comprising the step of comparing the concentration of the tracer compound in the sample with the concentration of tracer compound in a reference sample to determine the similarity of the sample to the reference sample.

12. A method as claimed in claim 11, wherein said comparison is carried out by comparing the absorbance of light at a wavelength between 500 and 510 nm of the chromophore solution made from the sample with a chromophore solution formed from the reference sample under the same conditions.

13. A method according to claim 9, wherein said urea solution comprises an aqueous solution of urea comprising from 30-35% of urea.

14. A method according to claim 13, wherein said aqueous solution of urea comprises a 32.5% aqueous solution of urea in accordance with the DIN70070 standard for urea solutions for SCR systems.

15. A method according to claim 9, wherein said tracer is selected from the group consisting of phenol, an alkyl phenol, an alkoxy phenol, a hydroxyphenol, and mixtures thereof.

16. A method of comparing a target sample of an aqueous urea solution with a reference sample of an aqueous urea solution containing a known concentration of a tracer composition comprising a tracer, said method comprising the steps of:
   a) reacting said reference sample with a reagent containing a predetermined amount of 4-aminoantipyrine in the presence of an initiating compound such that the reaction between the reagent and the tracer composition comprising the tracer in the liquid produces a chromophore, and measuring the absorbance of light of the resulting solution of the chromophore prepared from the reference sample,
   b) reacting said target sample with a reagent containing a pre-determined amount of 4-aminoantipyrine in the presence of an initiating compound such that the reaction between the reagent and the tracer composition comprising the tracer in the liquid produces a chromophore, measuring the absorbance of light of the resulting solution of the chromophore prepared from the target sample, and
   c) comparing the absorbance of light of the resulting solution of the chromophore prepared from the target sample with the absorbance of light of the resulting solution of the chromophore prepared from the reference sample to determine the similarity of the target sample to the reference sample,
wherein said tracer has the following structure:

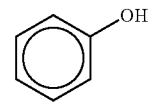

wherein any of carbon numbers 2-6 of the phenyl group may optionally be substituted.

17. A method as claimed in claim 16, wherein step (a) is not performed each time a target sample is analysed.

18. A method as claimed in claim 16, wherein step (a) is not performed and the absorbance of light of the resulting solution of the chromophore prepared from the target sample is compared with a pre-determined absorbance measurement from a standard reference sample.

19. A method according to claim 16, wherein said urea solution comprises an aqueous solution of urea comprising from 30-35% of urea.

20. A method according to claim 19, wherein said aqueous solution of urea comprises a 32.5% aqueous solution of urea in accordance with the DIN70070 standard for urea solutions for SCR systems.

21. A method according to claim 16, wherein said tracer is selected from the group consisting of phenol, an alkyl phenol, an alkoxy phenol, a hydroxyphenol, and mixtures thereof.

* * * * *